United States Patent [19]

Buess et al.

[11] Patent Number: 4,615,332

[45] Date of Patent: Oct. 7, 1986

[54] FLEXIBLE MULTICHANNEL ENDOSCOPE HAVING AXIAL SHAFT PORTIONS OF DIFFERENT FLEXIBILITY

[75] Inventors: Gerd Buess, Pulheim; Siegfried Hiltebrandt, Knittlingen; Manfred Boebel, Oetisheim, all of Fed. Rep. of Germany

[73] Assignee: Richard Wolf GmbH, Fed. Rep. of Germany

[21] Appl. No.: 711,754

[22] Filed: Mar. 14, 1985

[30] Foreign Application Priority Data

Mar. 30, 1984 [DE] Fed. Rep. of Germany ....... 3411767

[51] Int. Cl.[4] .............................................. A61B 1/06
[52] U.S. Cl. ...................................................... 128/6
[58] Field of Search ...................... 128/4, 5, 6, 7, 673, 128/675

[56] References Cited

U.S. PATENT DOCUMENTS

| | | | |
|---|---|---|---|
| 1,551,770 | 9/1925 | Palmeter | 128/6 |
| 4,061,135 | 12/1977 | Widran et al. | 128/6 |
| 4,102,333 | 7/1978 | Storz | 128/6 |
| 4,146,019 | 3/1979 | Bass et al. | 128/6 |
| 4,210,029 | 7/1980 | Porter | 128/673 X |
| 4,349,014 | 9/1982 | Takamatsu | 128/6 |
| 4,430,996 | 2/1984 | Bonnet | 128/4 X |

*Primary Examiner*—William H. Grieb
*Attorney, Agent, or Firm*—Hill, Van Santen, Steadman & Simpson

[57] ABSTRACT

A flexible or partially flexible endoscope comprising several passages and image guides passing through the shaft has the features that its distal omnilaterally steerable shaft is proximally constructed semirigidly or rigidly, is secured in a coupling element situated on the control housing and is traversed by several image guides which have allocated to them at the proximal control housing several monoculars and/or binoculars via rigid or flexible longitudinal elements. It is possible thereby to replace numerous separate endoscopes by a single endoscope.

5 Claims, 3 Drawing Figures

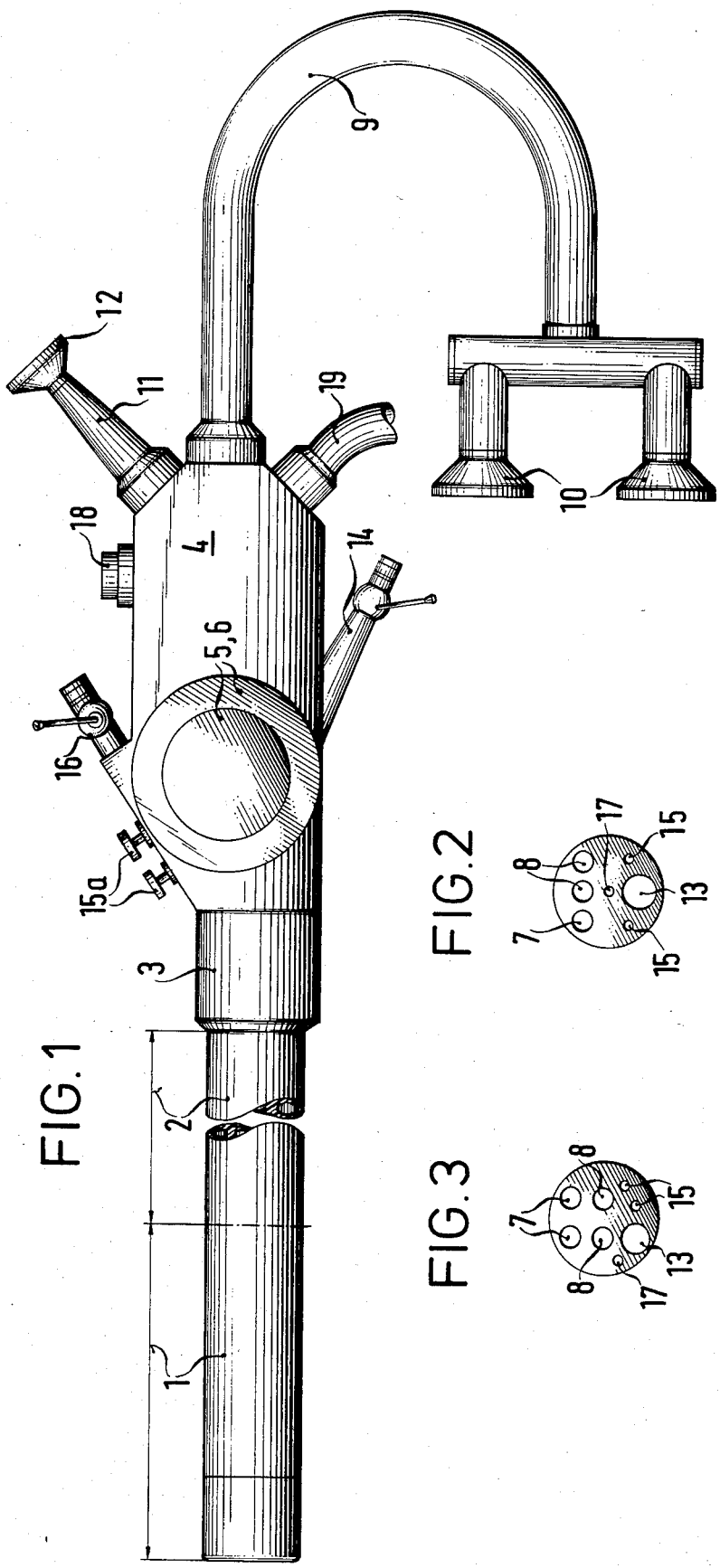

4,615,332

FLEXIBLE MULTICHANNEL ENDOSCOPE HAVING AXIAL SHAFT PORTIONS OF DIFFERENT FLEXIBILITY

BACKGROUND OF THE INVENTION

1. Field of the Invention

The invention relates to a flexible or partially flexible endoscope comprising several passages and image guides passing through the shaft.

2. Description of the Prior Art

Until now, the procedure followed in endoscope technology has been such that a special endoscope design was produced and utilised for each purpose of application, which was adapted to this purpose, so that a plurality of endoscopes was required for utilization.

SUMMARY OF THE INVENTION

It is an object of the invention to construct an endoscope in such a manner that it is applicable for different purposes in the inspection of and/or operations within bodily cavities.

In accordance with the invention, this object is achieved in an endoscope of the type referred to in the foregoing, in that a distally omnilaterally steerable shaft has a semirigid or rigid proximal end secured in a coupling element situated on a control housing, and is traversed by a plurality of image guides, which have allocated to them at the proximal control housing several monoculars or binoculars to which they are connected via rigid or flexible longitudinal elements.

An endoscope of this nature may be utilised for different observational and operational purposes and replaces several individual endoscopes which had otherwise been needed for these different purposes and above all provides the operator as well as a co-observer with clear and sharp pictures, whilst making observation available to the physician under free and unimpeded movement of the oculars. To this end, a separate fibre optic guide is set aside for each ocular.

BRIEF DESCRIPTION OF THE DRAWINGS

The invention is described in the following with reference to the drawings wherein an example of embodiment is illustrated. In these:

FIG. 1 shows the endoscope in accordance with the invention, with separate illustration of the distal shaft section in plan view, FIG. 2 shows an end view of the distal shaft extremity, FIG. 3 shows an end view of the distal shaft extremity in an embodiment modified as compared to FIG. 2.

DETAILED DESCRIPTION OF THE PREFERRED EMBODIMENTS

According to the example shown in the drawings, the shaft of the endoscope is divided into a steerable distal length 1 and a resiliently bendable or rigid shaft length 2, which may have their longitudinal ratio selected at will. The shaft 1, 2 is connected by means of a known coupling 3 to a control housing 4. The distal shaft extremity 1 is omnilaterally steerable by means of handles 5, 6 of the control housing 4.

According to FIGS. 1 and 2, the shaft 1, 2 and the control housing 4 are traversed by three fibre optic image guides 7 and 8, whereof the two image guides 8 are led separately at the proximal side via a flexible longitudinal element 9 of the image guides to the two oculars of a binocular 10, and the image guide 7 is led via a rigid or equally flexible longitudinal element 11 to a monocular 12 for a co-observer or for a connectible camera.

If two each of guides 7 and 8 extend through the shaft 1, 2 according to FIG. 3, the monocular 12 can equally be replaced by binoculars. Matters may also be so organised that the binoculars 10 are a monocular, and the monocular 12 is a pair of binoculars. The monocular 12 together with the image guide element 11 may be coupled as well as released to and from the control housing 4 by means of a coupling. It is also possible furthermore, to join the flexible longitudinal element 9 in fixed or connectible manner to the control housing 4.

The shaft 1, 2 is also equipped with a passage 13 through which auxiliary instruments may be inserted into a bodily cavity via the connector 14 of the control housing.

The shaft 1, 2 is traversed moreover by passages 15 for fluids or gases intended to be fed in and drained via the connectors 16. The bores of the passages 15 may be controlled manually by means of valves 15a. Finally, the distal shaft extremity 1 has situated thereat a pressure sensor 17 from which signals induced during pressure changes within the bodily cavity control a pneumatic device via a connection 18, which thereupon regulates the gas pressure within the bodily cavity via the connectors 16.

The volume of the shaft 1, 2 between the image guides and the passages is occupied by a fibre light guide which may be joined to a light projector via a connection and a flexible cable 19.

To ease the physician's work with the endoscope, the binoculars 10 may for example be immobilised in front of the physician's eyes by means of a headband, and the control housing may be stationarily supported by means of the coupling connector 3, via bearers.

What is claimed is:

1. In an endoscope having a flexible shaft with a plurality of channels and image conductors extending the length of the shaft, the improvement comprising the shaft having an omnilaterally steerable flexible distal end portion and a proximal end portion of a higher rigidity than the flexible distal end portion, a control housing, a coupling element connecting the proximal end portion of the shaft to the control housing, said shaft having at least three image conductors extending therethrough from the distal end and into the control housing, a binocular eye piece, a flexible element containing image conductors extending from the control housing to the binocular eye piece and being connected to two of the image conductors extending into the control housing and the remaining image conductor being connected to an auxiliary eye piece.

2. In an endoscope according to claim 1, wherein said auxiliary eye piece is a monocular eye piece releasably secured to said control housing.

3. In an endoscope according to claim 1, further comprising a pressure sensor situated at the distal end of the shaft for measuring the prevailing bodily cavity pressure, said sensor being arranged to control a pneumatic device for regulating the bodily cavity pressure via a connection of the control housing.

4. Endoscope according to claim 1, wherein the coupling element is releasably secured by means of supports for holding the control housing.

5. An endoscope comprising a shaft having an omnilaterally steerable flexible distal end portion and a proximal portion of higher rigidity than said flexible distal end portion, a control housing;

a coupling element connecting a proximal end of said shaft to said control housing;

control means operable from said control housing to steer said distal end portion of the shaft;

at least one axial passage extending through said shaft for an auxiliary instrument, and a connector on said housing to provide access to said passage;

at least one axial fluid passage extending through said shaft for feeding and draining fluids, said fluid passage communicating with a connector on said housing and at least one valve being provided on said housing to control the flow of said fluids in the fluid passage;

a pressure sensor at a distal end of said shaft to detect pressure changes in a body cavity, said sensor being pneumatically connected to proximal pressure-regulating means for said body cavity;

fibre light guide means to guide light from a proximal source axially through said shaft to the distal end thereof;

at least three fibre optic image guides extending axially through said shaft and a plurality of eyepieces being connected to the proximal ends of said image guides, two of said image guides being connected to a binocular eyepiece via a flexible connecting element which extends axially rearwardly from said housing, and a third image guide being connected to a monocular eyepiece via a rigid connecting element projecting obliquely from said housing.

* * * * *